United States Patent
Corcoran et al.

(10) Patent No.: US 7,691,115 B2
(45) Date of Patent: Apr. 6, 2010

(54) OCCLUSION DEVICE WITH FLEXIBLE FABRIC CONNECTOR

(75) Inventors: Michael P. Corcoran, Woodbury, MN (US); Joseph A. Marino, Apple Valley, MN (US)

(73) Assignee: Cardia, Inc., Eagan, MN (US)

( * ) Notice: Subject to any disclaimer, the term of this patent is extended or adjusted under 35 U.S.C. 154(b) by 660 days.

(21) Appl. No.: 11/455,413

(22) Filed: Jun. 19, 2006

(65) Prior Publication Data

US 2007/0293889 A1    Dec. 20, 2007

(51) Int. Cl.
*A61B 17/08* (2006.01)
(52) U.S. Cl. .................... 606/157; 606/213
(58) Field of Classification Search ............ 606/151, 606/157, 158, 213
See application file for complete search history.

(56) References Cited

U.S. PATENT DOCUMENTS

| | | | |
|---|---|---|---|
| 3,874,388 A | 4/1975 | King et al. | |
| 4,007,743 A | 2/1977 | Blake | |
| 4,284,166 A | 8/1981 | Gale | |
| 4,917,089 A | 4/1990 | Sideris | |
| 5,092,424 A | 3/1992 | Schreiber et al. | |
| 5,108,420 A | 4/1992 | Marks | |
| 5,171,259 A | 12/1992 | Inoue | |
| 5,284,488 A * | 2/1994 | Sideris | 606/213 |
| 5,334,137 A | 8/1994 | Freeman | |
| 5,334,217 A | 8/1994 | Das | |
| 5,382,260 A | 1/1995 | Dormandy, Jr. et al. | |
| 5,397,331 A | 3/1995 | Himpens et al. | |
| 5,425,744 A | 6/1995 | Fagan et al. | |
| 5,433,727 A | 7/1995 | Sideris | |
| 5,451,235 A | 9/1995 | Lock et al. | |
| 5,634,936 A | 6/1997 | Linden et al. | |
| 5,702,421 A | 12/1997 | Schneidt | |
| 5,709,707 A | 1/1998 | Lock et al. | |
| 5,725,552 A | 3/1998 | Kotula et al. | |
| 5,741,297 A | 4/1998 | Simon | |
| 5,904,703 A | 5/1999 | Gilson | |
| 5,944,738 A * | 8/1999 | Amplatz et al. | 606/213 |
| 6,024,756 A | 2/2000 | Huebsch et al. | |
| 6,174,322 B1 | 1/2001 | Schneidt | |
| 6,206,907 B1 | 3/2001 | Marino et al. | |
| 6,389,146 B1 | 5/2002 | Croft, III | |
| 6,551,344 B2 | 4/2003 | Thill | |
| 6,634,455 B1 | 10/2003 | Yang | |
| 6,656,206 B2 * | 12/2003 | Corcoran et al. | 606/213 |
| 2002/0111647 A1 | 8/2002 | Khairkhahan et al. | |

FOREIGN PATENT DOCUMENTS

| | | |
|---|---|---|
| DE | 42 22 291 C1 | 1/1994 |
| EP | 0 362 113 | 4/1993 |
| EP | 0 541 063 | 9/1998 |
| GB | 2 269 321 A | 9/1994 |

* cited by examiner

*Primary Examiner*—(Jackie) Tan-Uyen T Ho
*Assistant Examiner*—Melissa Ryckman
(74) *Attorney, Agent, or Firm*—Kinney & Lange, P.A.

(57) ABSTRACT

An occlusion device includes a center assembly having a flexible section formed by a fabric connector. The flexible fabric connector gives the center assembly improved flexure characteristics, which allows the occlusion device to better conform to the contours of the heart.

11 Claims, 5 Drawing Sheets

OCCLUSION DEVICE WITH FLEXIBLE FABRIC CONNECTOR

BACKGROUND OF THE INVENTION

This invention relates to an occlusion device for repairing cardiovascular defects. More specifically, this invention relates to an occlusion device which has a center assembly including a flexible fabric connector that provides improved flexure characteristics and allows the device to better conform to the contours of the heart.

Normally, permanently repairing certain cardiac defects in adults and children requires open heart surgery, a risky, expensive, and painful procedure. To avoid the risks and discomfort associated with open heart surgery, occlusion devices have been developed that are small, implantable devices capable of being delivered to the heart through a catheter. Rather than surgery, a catheter inserted into a major blood vessel allows an occlusion device to be deployed by moving the device through the catheter. This procedure is performed in a cardiac cathlab and avoids the risks and pain associated with open heart surgery. These occlusion devices can repair a wide range of cardiac defects, including patent foramen ovale, patent ductus arteriosus, atrial septal defects, ventricular septal defects, and may occlude other cardiac and non-cardiac apertures. There are currently several types of occlusion devices capable of being inserted via a catheter. The occlusion devices must have sufficient flexibility to accomplish the sharp and numerous turns in the body's vasculature.

Another challenge in deploying an occlusion device in the heart is the variations of the contours of the aperture the occlusion device is meant to close. In particular, when occluding septal defects, the uneven topography in the vascular and septal walls of the human heart makes it difficult to design a device that can adapt to such variations. The challenge in designing an occluder which conforms to the uneven topography is compounded by the fact that the contours of each defect in each individual patient are unique. Poor conformation to the defect results in poor seating of the occlusion device across the aperture, which decreases the ability of the device to successfully occlude the aperture.

Lack of conformation to the walls of the heart can place significant amounts of stress on the occlusion device and decrease fatigue life. Once deployed, different parts of the occluder may experience more or less stress as a result of the uneven topography. At some point, stressed parts of the occluder may break. Broken parts increase the likelihood of damage to the surrounding tissue and lead to patient anxiety.

Thus, there is a need in the art for an occlusion device that will occlude cardiac defects and will match the contours of the heart thereby increasing the life of the device and its sealing ability while reducing damage to the surrounding tissue.

BRIEF SUMMARY OF THE INVENTION

The present invention is an occlusion device having a center assembly that includes a flexible fabric connector. The occlusion device has a first occluding body and a second occluding body connected by the center assembly. The center assembly comprises a proximal hub, which is attached to the first occluding body, a distal hub, which is attached to the second occluding body, and a flexible fabric connector extending between the proximal hub and the distal hub. The flexible fabric connector increases the ability of the occlusion device to more accurately conform to the defect, while still allowing the device to be moved, deployed and retrieved using a catheter.

DETAILED DESCRIPTION

Figure 1A:
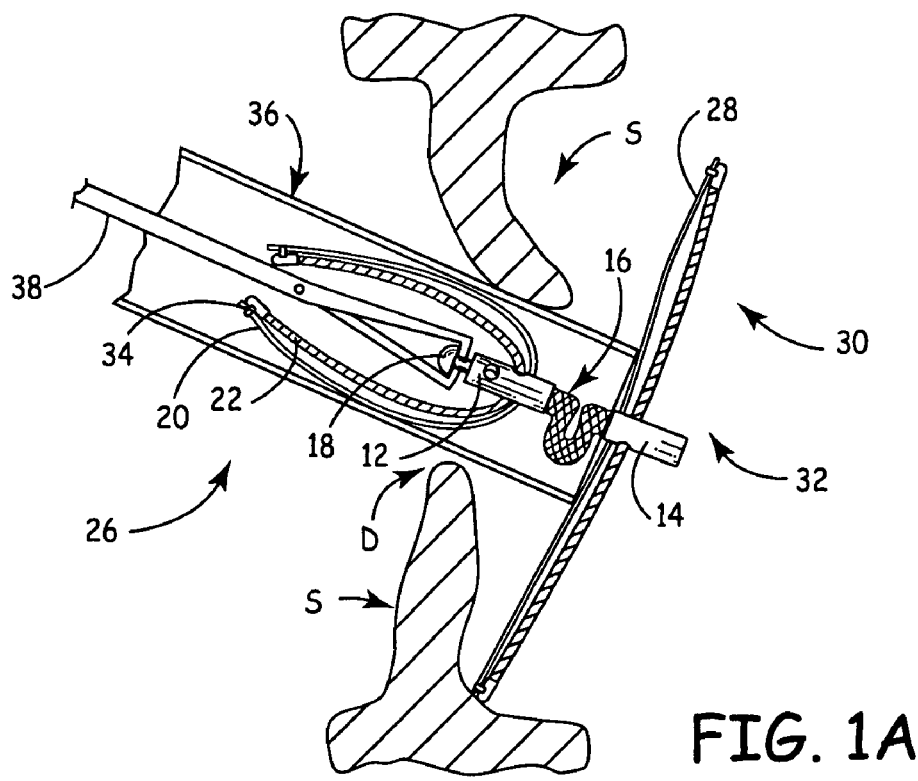
FIG. 1A-1B are diagrams of an occlusion device with a center assembly that includes a flexible fabric connector being inserted into a defect.
Figure 1B:
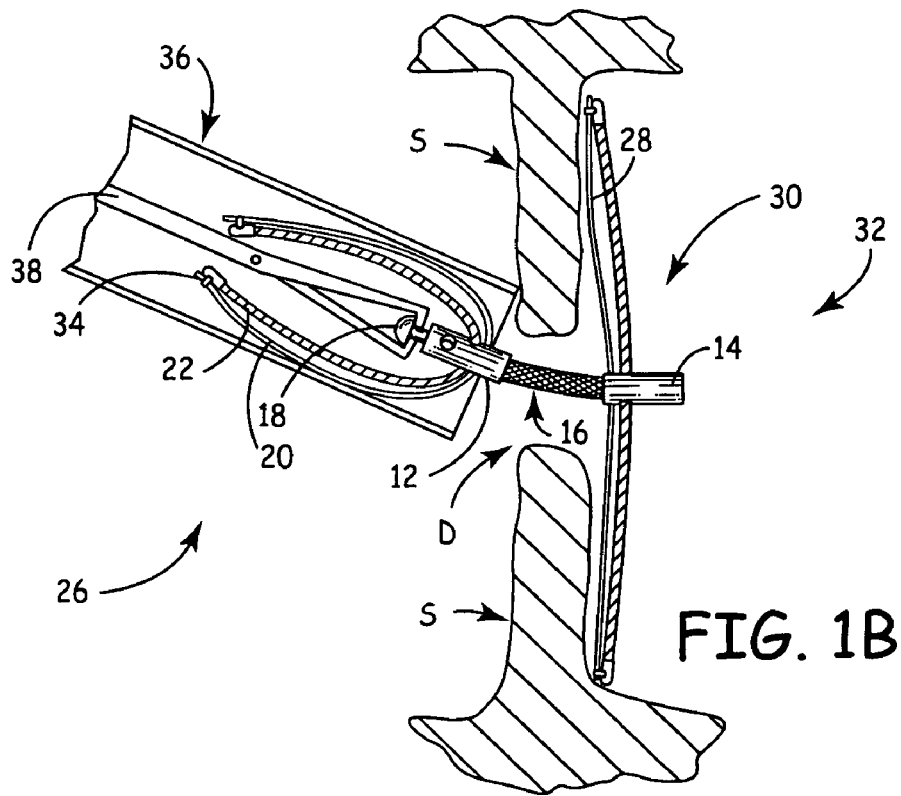

FIG. 1A-1B illustrate how occlusion device 10 having flexible fabric connector 16 is deployed. Occlusion device 10 includes proximal hub 12, distal hub 14, flexible fabric connector 16, knob 18, proximal support frame 20 and proximal sheet 22 (which form proximal occluding body 26), distal support frame 28 and distal sheet 30 (which form distal occluding body 32), and atraumatic tips 34. Also, shown are septal wall S, septal defect D, catheter 36, and delivery forceps 38.

Flexible fabric connector 16 extends between proximal hub 12 and distal hub 14 to form a center assembly. (Methods of attaching flexible fabric connector 16 to proximal and distal hubs 12,14 will be discussed in detail with reference to FIGS. 2-4.) Proximal and distal hubs 12,14 may be comprised of any suitable material, including Nitinol (a nickel-titanium alloy), titanium or stainless steel. Flexible fabric connector 16 may also be formed of any suitable material, including polyvinyl alcohol (PVA), polypropylene, polyester, such as that offered under the trademark DACRON®, and polytetrafluoroethylene (PTFE), such as that offered under the trademark TEFLON®. Flexible fabric connector 16 is preferably formed to have a diameter of less than about 5 millimeters. In addition, the length of flexible fabric connector 16 is preferably less than about 20 millimeters.

Proximal and distal support frames 20,28 are attached to sheets 22,30 in any suitable manner, such as with sutures or by molding sheets 22,30 directly around proximal and distal support frames 20,28 to form proximal occluding body 26 and distal occluding body 32. Proximal and distal support frames 20,28 may be comprised of any number of arms (although only one arm of each of frames 20 and 28 can be seen in FIG. 1). One method of connecting the arms to proximal and distal hubs 12, 14 is to provide proximal and distal hubs 12, 14 with drill holes through which the arms extend. Atraumatic tips 34 are located at the distal end of each arm and serve to minimize damage to the surrounding tissue. Atraumatic tips 34 provide a place for sutures to attach sheets 22, 30 to proximal and distal support frames 20, 28. One method of suturing sheets 22, 30 to proximal and distal support frames 20, 28 is to provide atraumatic tips 34 with drill holes through which sutures pass. In this way, sheets 22,30 are sewn to support frames 20,28 at atraumatic tips 34. Proximal support frame 20 is connected to proximal hub 12. Distal support frame 28 is connected to distal hub 14.

More specifically, occlusion device 10 is constructed so that proximal and distal support frames 20,28 are easily collapsible about proximal and distal hubs 12, 14. Due to this construction, occlusion device 10 can be folded so that proximal and distal support frames 20,28 are folded in an axial direction. Proximal and distal sheets 22,30, which are attached to proximal and distal support frames 20,28, are flexible, and can likewise collapse as proximal and distal support frames 20, 28 are folded. In addition, proximal hub 12 further comprises knob 18, which allows for occlusion device 10 to be grasped by forceps 38 as it is inserted into the body through catheter 36.

Once occlusion device 10 is deployed, support frames 20,28 must serve to hold proximal and distal sheets 22,30 in place to seal defect D. To ensure there is sufficient tension to hold sheets 22,30 in place, support frames 20,28 are made of a suitable material capable of shape memory, such as Nitinol. Nitinol is preferably used because it is commercially available, very elastic, non-corrosive, and has a fatigue life greater than that of stainless steel or titanium. To further ensure that support frames 20, 28 do not suffer from fatigue failures, support frames 20,28 may be made of stranded wire or cables.

Sheets 22,30 are comprised of a medical grade polymer in the form of film, foam, gel, or a combination thereof. One suitable material is DACRON®. Another suitable material is polyurethane. Preferably, a high density polyvinyl alcohol (PVA) foam is used, such as that offered under the trademark IVALON®. To minimize the chance of occlusion device 10 causing a blood clot, foam sheets 22,30 may be treated with a thrombosis inhibiting material, such as heparin.

The size of sheets 22, 30 may vary to accommodate various sizes of defects. When measured diagonally, the size of sheets 22,30 may range from about 10 millimeters to about 45 millimeters. In some instances, it may be desirable to form sheets 22, 30 so that they are not both the same size. For instance, one sheet and its associated fixation device can be made smaller (25 millimeters) than the corresponding sheet and its associated fixation device (30 millimeters). This is particularly useful in situations where occlusion device 10 is to be placed at a location in the heart which is close to other nearby cardiac structures. Making sheets 22,30 different sizes may assist in providing optimal occlusion of a defect, without affecting other structures of the heart which may be nearby.

FIG. 1A illustrates occlusion device 10 being inserted into septal defect D, which is one example of a cardiac defect that may be occluded using occlusion device 10. Occlusion device 10 is being inserted into septal defect D from catheter 36. Occlusion device 10 is held by delivery forceps 38. To insert occlusion device 10, catheter 36 is positioned proximate septal defect D. Next, delivery forceps 38 is used to push occlusion device 10 through catheter 36 so that distal occluding body 32 unfolds in the left atrium. Although distal occluding body 32 has been deployed, proximal occluding body 26 is still folded in catheter 36.

The placement of catheter 36, or other means that guides occlusion device 10 to septal defect D, determines the location of and angle at which occlusion device 10 is deployed. Once catheter 36 is properly positioned at septal defect D, delivery forceps 38 is used to push occlusion device 10 through septal defect D. Distal occluding body 32 of occlusion device 10 is then allowed to expand against septal wall S surrounding septal defect D.

Fabric connector 16 is flexible but remains inside catheter 36 and is therefore immobilized. If fabric connector 16 of occlusion device 10 is not flexible (or flexible but immobilized), the center assembly must enter septal defect D following the same angle of insertion as catheter 36 or other delivery device. As a result, the insertion angle is limited by the catheter's angle of insertion.

Often, due to limited space, catheter 36 enters the heart at an angle that is not perpendicular to septal wall S. In this situation, occlusion device 10 cannot enter septal defect D properly because the line of the center assembly must follow the same line as catheter 36. Occlusion device 10 must be forced into septal defect D at an angle, which may cause the tissue surrounding septal defect D to become distorted. If the surrounding cardiac tissue is distorted by catheter 36, it is difficult to determine whether occlusion device 10 will be properly seated once catheter 36 is removed and the tissue returns to its normal state. If occlusion device 10 is not seated properly, blood will continue to flow through septal defect 32 and occlusion device 10 may have to be retrieved and redeployed. Both doctors and patients prefer to avoid retrieval and re-deployment because it causes additional expense and longer procedure time.

FIG. 1B shows occlusion device 10 with flexible fabric connector 16 being inserted into defect D. In FIG. 1B, occlusion device 10 has been further advanced through catheter 36 to expose flexible fabric connector 16.

Because fabric connector 16 is flexible, the insertion angle of occlusion device 10 is not restricted to that of catheter 36. Occlusion device 10 can be easily inserted, because once flexible fabric connector 16 is outside catheter 36, the angle of insertion can be changed by allowing flexible fabric connector 16 to move. This variable insertion angle allows occlusion device 10 to enter defect D at an optimum angle, minimizing distortion of surrounding cardiac tissue. If the tissue is not distorted when occlusion device 10 is deployed, the seating of occlusion device 10 should not change drastically once catheter 36 is removed. Because occlusion device 10 can be properly seated at the first insertion, the number of cases that require retrieval and redeployment should decrease.

Figure 1C:
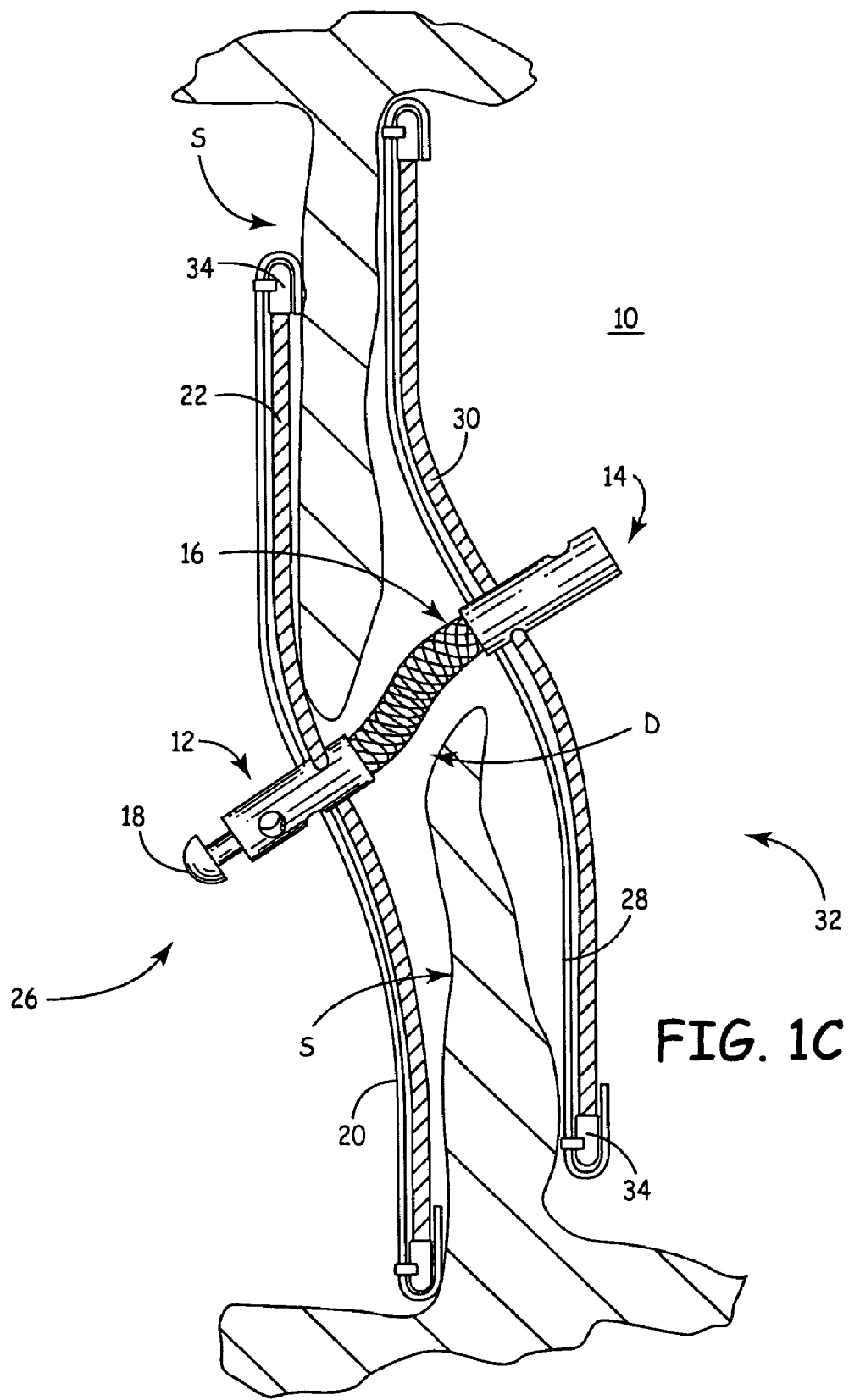
FIG. 1C is a diagram demonstrating the conformation capabilities of the occlusion device of FIGS. 1A-1B.

FIG. 1C shows occlusion device 10, which is fully deployed and is occluding defect D. Shown is occlusion device 10, which includes proximal hub 12, distal hub 14, flexible fabric connector 16, knob 18, proximal support frame 20 and proximal sheet 22 (which form proximal occluding body 26), distal support frame 28 and distal sheet 30 (which form distal occluding body 32), and atraumatic tips 34. Also, shown are septal wall S, septal defect D, catheter 36, and delivery forceps 38.

By forming at least a portion of the center assembly to include flexible fabric connector 16, the seating ability of occlusion device 10 is improved without the need for increased arm tension, which is necessary to occlude septal defect D or functionality (i.e. ability to move through a catheter, to twist or turn during deployment, to place against a septal wall) needed to properly deploy occlusion device 10.

Flexible fabric connector 16 has no negative effect on the ability to move occlusion device 10 through catheter 36. This is because the length of fabric connector 16 is preferably less than about 20 millimeters and is extremely flexible. As such, when flexible fabric connector 16 experiences pushing forces, such as when proximal and distal hubs 12, 14 are pushed toward one another when occlusion device 10 is moved through catheter 36, flexible fabric connector 16 collapses and proximal and distal hubs 12, 14 butt up against each other, which enables occlusion device 10 to be manipulated in a forward direction. Flexible fabric connector 16 also has sufficient pull strength to allow occlusion device 10 to be manipulated in a backward direction.

At the same time, flexible fabric connector 16 is capable of flexure. When flexible fabric connector 16 is not being pushed or pulled or is not experiencing resistance, flexible fabric connector 16 is extremely flexible. This flexibility of fabric connector 16 allows for occlusion device 10 to be moved easily through sharp turns in a catheter, and allows for occlusion device 10 to be placed so that one side of occlusion device 10 is easily flexible relative to the other side.

Further, once deployed, flexible fabric connector 16 is strong enough to hold proximal and distal occluding bodies 26,32 of occlusion device 10 in place. Thus, flexible fabric connector 16 provides the functionality required to deploy occlusion device 10, while offering the benefits of a fully flexible center connector.

In FIG. 1C, distal occluding body 32 has been properly positioned, proximal occluding body 26 has been deployed and occlusion device 10 has been released. FIG. 1C also demonstrates the ability of occlusion device 10 with flexible fabric connector 16 to conform to an irregularly shaped septal defect D.

Another important advantage of the present invention is that flexible fabric connector 16 allows distal and proximal occluding bodies 26,32 to conform more readily to the contours of a heart after it is deployed, providing a custom fit to a variety of defects. Often, when implanted, occlusion device 10 is located in an irregularly shaped defect. Having flexible fabric connector 16 allows occlusion device 10 to conform to a broader spectrum of defects.

For instance, as viewed in FIG. 1C, septal wall S on the bottom of septal defect D may be only a few millimeters thick, but septal wall S on the top of septal defect D may be much thicker. In such cases, one side of occlusion device 10 may be bent open further than the other side. The side that is more distorted carries a high static load which increases pressure on the surrounding tissue and also increases the possibility of device fracture or septal tissue perforation. Because fabric connector 16 is flexible, it can bend such that proximal and distal support frames 20,28 need not be the only the only parts which adjust to fit septal defect D. The ability to conform to a variety of heart contours results in better seating, reduces arm tension (increasing fatigue life), and decreases the likelihood of damage to tissue resulting from breakage and from device fracture.

Another feature of occlusion device 10 is that it is fully retrievable. To allow occlusion device 10 to be retrievable, as well as ensure that occlusion device 10 fits into a small diameter catheter, it is important to ensure that the arms of support frames 20,28 are not of a length that results in atraumatic tips 34 clustering at the same location. If atraumatic tips 34 all cluster at the same location when occlusion device 10 is inside catheter 36, occlusion device 10 will become too bulky to allow it to be easily moved through catheter 36.

Figure 2:
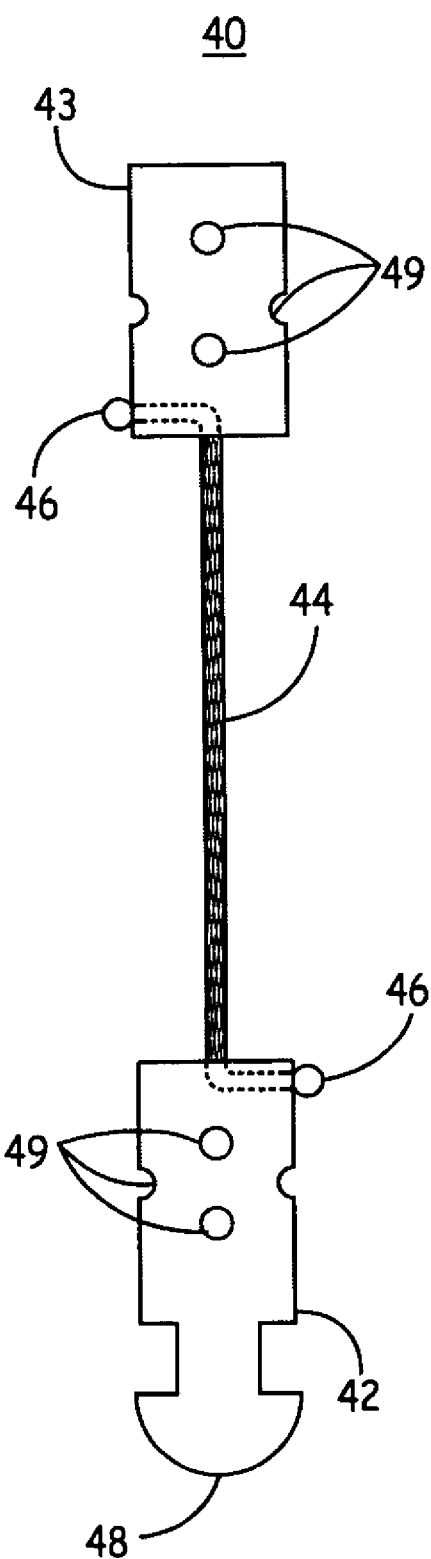
FIG. 2 is a first embodiment of a center assembly comprising a single braided fabric thread for use in an occlusion device.

FIG. 2 is a first embodiment of center assembly 40 for use in an occlusion device. Center assembly 40 includes proximal hub 42, distal hub 43 and flexible fabric connector 44. Also shown are knots 46, grasping knob 48, and holes 49, which provide a location for attaching occluding bodies, such as the wire support frames (shown in FIG. 1) to proximal and distal hubs 42, 43.

As shown in FIG. 2, flexible fabric connector 44 is comprised of a single braided fabric thread and extends between proximal hub 42 and distal hub 43 to form center assembly 40. Proximal and distal hubs 42,43 may be comprised of any suitable material, including Nitinol (a nickel-titanium alloy), titanium or stainless steel. Flexible fabric connector 44 may also be formed of any suitable material, including polyvinyl alcohol (PVA), polypropylene, polyester, such as that offered under the trademark DACRON®, and polytetrafluroethylene (PTFE), such as that offered under the trademark TEFLON®. Flexible fabric connector 44 is preferably formed to have a diameter of less than about 5 millimeters. In addition, the length of flexible fabric connector 54 is preferably less than about 20 millimeters.

Center assembly 40 may be assembled by providing the distal end of proximal hub 42 and the proximal end of distal hub 43 with cavities or drill holes and threading an first end of flexible fabric connector 44 though proximal hub 42 and a second end of flexible fabric connector 44 though distal hub 43. Flexible fabric connector 44 is secured to an outside surface of proximal and distal hubs 42 and 43 with knots 46. However, flexible fabric connector 44 may be attached to proximal and distal hubs 42 and 43 with any suitable method. For instance, a crimp ring or collar could also be used to attach flexible fabric connector 44 to proximal and distal hubs 42 and 43.

Figure 3:
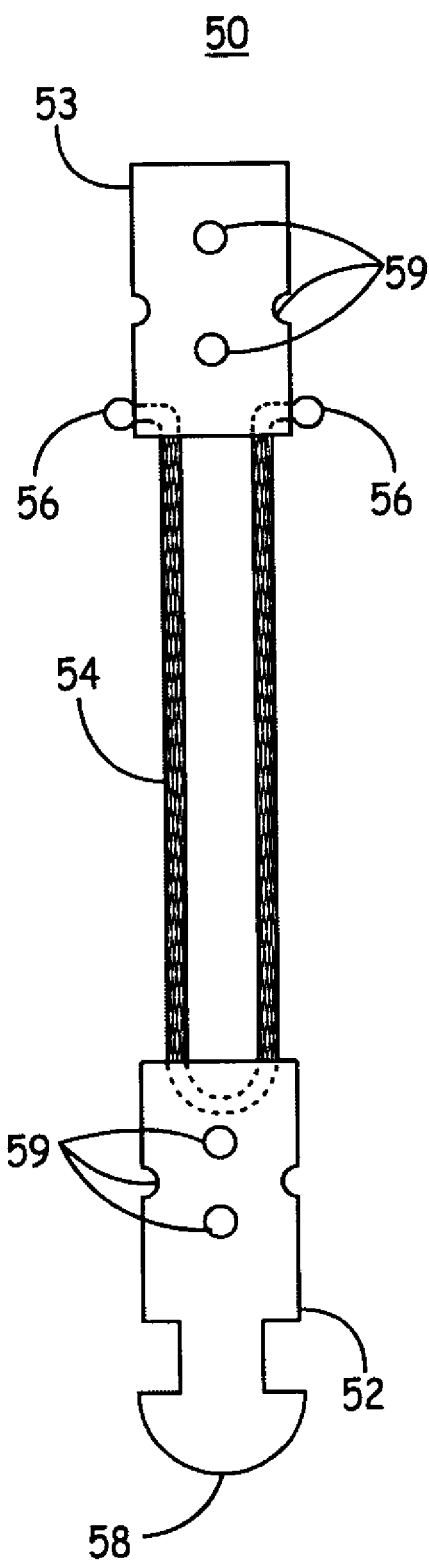
FIG. 3 is a second embodiment of a center assembly comprising a braided fabric thread that forms a loop for use in an occlusion device.

FIG. 3 is a second embodiment of center assembly 50 for use in an occlusion device. Center assembly 50 includes proximal hub 52, distal hub 53 and flexible fabric connector 54. Also shown are knots 56, grasping knob 58, and holes 59, which provide a location for attaching occluding bodies, such as the wire support frames (shown in FIG. 1) to proximal and distal hubs 52, 53.

As shown in FIG. 3, flexible fabric connector 54 is comprised of a single braided fabric thread, which forms one loop and extends between proximal hub 52 and distal hub 53 to form center assembly 50. (Although only one loop is shown, flexible fabric connector 54 may include any number of loops.) Proximal and distal hubs 52,53 maybe comprised of any suitable material, including Nitinol (a nickel-titanium alloy), titanium or stainless steel. Flexible fabric connector 54 may also be formed of any suitable material, including polyvinyl alcohol (PVA), polypropylene, polyester, such as that offered under the trademark DACRON®, and polytetrafluoroethylene (PTFE), such as that offered under the trademark TEFLON®. Flexible fabric connector 54 is preferably formed to have a diameter of less than about 5 millimeters. In addition, the length of flexible fabric connector 54 is preferably less than about 20 millimeters.

Center assembly 50 may be assembled by providing the distal end of proximal hub 52 with a set of drill holes or an external loop and the proximal end of distal hub 53 with two sets of cavities or drill holes. Flexible fabric connector 54 is threaded though proximal hub 52 and first and second ends of flexible fabric connector 54 are threaded though distal hub 53 and secured to an outside surface of distal hub 53 with knots 56 to form a loop. However, flexible fabric connector 54 may be attached to proximal and distal hubs 52 and 53 with any suitable method. For instance, after flexible fabric connector 54 is threaded though proximal hub 52, a crimp ring or collar could also be used to attach flexible fabric connector 54 to proximal hub and/or distal hub 53.

Figure 4:
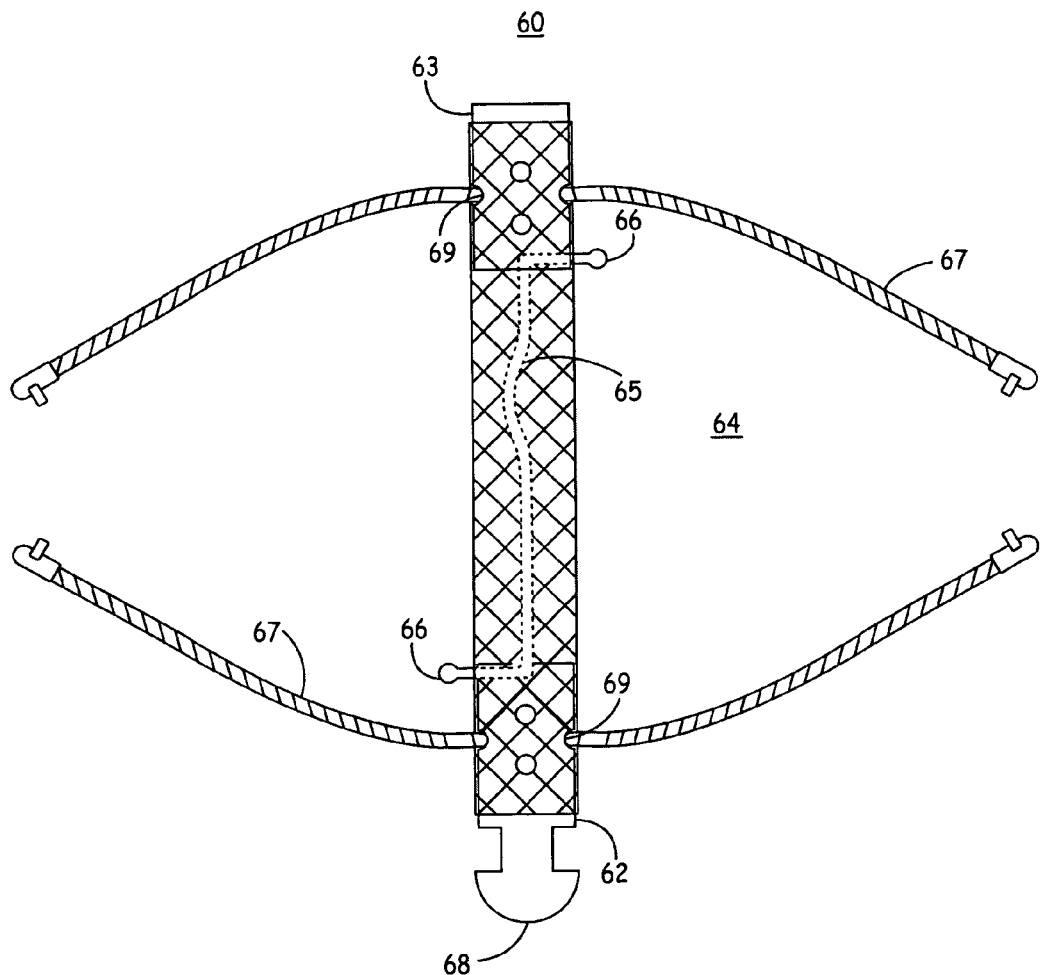
FIG. 4 is a partial cross sectional view of a third embodiment of a center assembly comprising a braided fabric tube and a safety tether for use in an occlusion device.

FIG. 4 is partial cross sectional view of a third embodiment of center assembly 60 for use in an occlusion device. Center assembly 60 includes proximal hub 62, distal hub 63 and flexible fabric connector 64. Also shown is safety tether 65, knots 66, arms 67, grasping knob 68, and holes 69, which provide a location for attaching arms 67.

As shown in FIG. 4, flexible fabric connector 64 is comprised of a braided fabric tube, which extends between proximal hub 62 and distal hub 63 to form center assembly 60. Proximal and distal hubs 62,63 may be comprised of any suitable material, including Nitinol (a nickel-titanium alloy), titanium or stainless steel. Flexible fabric connector 64 may also be formed of any suitable material, including polyvinyl alcohol (PVA), polypropylene, polyester, such as that offered under the trademark DACRON®, and polytetrafluoroethylene (PTFE), such as that offered under the trademark TEFLON®. Flexible fabric connector 64 is formed by braiding a plurality of fabric threads into a tube and is has a diameter of less than about 5 millimeters. In addition, the length of flexible fabric connector 64 is preferably less than about 20 millimeters.

One method of attaching flexible fabric connector 64 to proximal and distal hubs 62, 63 is to insert proximal and distal hubs 62, 63, which are sized to correspond to an overall diameter of flexible fabric connector 64, into the proximal and distal ends of flexible fabric connector 64. Flexible fabric connector 64 is provided with holes, which correspond to holes 69 of proximal and distal hubs 62,63. As shown in FIG. 4, arms 67 are inserted through flexible fabric connector 64 into holes 69 to secure flexible fabric connector 64 in place. Other assembly methods include using a collar or pin to secure flexible fabric connector 64 to proximal hub 62 and distal hub 63.

Center assembly 60 also includes safety tether 65, which serves to further ensure the structural integrity of center assembly 60. Safety tether 65 connects proximal hub 62 to distal hub 63 and extends through the middle of flexible fabric connector 64. Safety tether 65 may be attached to proximal and distal hubs 62,63 by providing the distal end of proximal hub 62 and the proximal end of distal hub 63 with cavities or drill holes and threading an first end of safety tether 65 though proximal hub 62 and a second end of safety tether 65 though distal hub 63. Safety tether 65 is secured to an outside surface of proximal and distal hubs 62, 63 with knots 66.

Safety tether 65 ensures that center assembly 60 remains fully connected while navigating the vasculature of a body and during deployment in a heart. Safety tether 65 also increases the pull strength of flexible fabric connector 64 which is important because in order for an occlusion device to be retrieved, it must be pulled back through a catheter.

Safety tether 65 may be comprised of any suitable material, including Nitinol, titanium, stainless steel or polymeric material. In addition, safety tether 65 may be comprised of a single wire or thread or safety tether 65 may be comprised of a multi-wire strand or cable or a multi-thread fabric braid.

Although the present invention has been described with reference to preferred embodiments, workers skilled in the art will recognize that changes may be made in form and detail without departing from the spirit and scope of the invention.

The invention claimed is:

1. An occlusion device comprising:
   a first occluding body;
   a second occluding body; and
   a center assembly comprising a proximal hub attached to the first occluding body, a distal hub attached to the second occluding body, a flexible tubular fabric connector having a proximal end attached to the proximal hub and having a distal end attached to the distal hub, and a safety tether extending through a center of the flexible tubular fabric connector between the proximal hub and the distal hub, wherein the safety tether has a proximal end attached to the proximal hub and a distal end attached to the distal hub, wherein the proximal end of the safety tether extends through the proximal hub and out a side of the proximal hub and the distal end of the safety tether extends through the distal hub and out a side of the distal hub.

2. The occlusion device of claim 1 wherein an overall diameter of the flexible fabric connector is less than about 5 millimeters.

3. The occlusion device of claim 1 wherein the safety tether comprises a wire.

4. The occlusion device of claim 1 wherein the safety tether comprises a braided fabric.

5. The occlusion device of claim 1 wherein the flexible tubular fabric connector comprises a single braided fabric strand extending between the proximal hub and the distal hub.

6. The occlusion device of claim 1 wherein the flexible tubular fabric connector is braided.

7. The occlusion device of claim 1 wherein the proximal end of the safety tether has a knot located on the side of the proximal hub, and the distal end of the safety tether has a knot located on the side of the distal hub.

8. The occlusion device of claim 1 wherein the flexible tubular fabric connector extends over at least a portion of both the proximal hub and the distal hub.

9. The occlusion device of claim 1 wherein the first occluding body includes a plurality of arms extending outwardly from the proximal hub and the second occluding body includes a plurality of arms extending outwardly from the distal hub.

10. The occlusion device of claim 6 wherein the flexible tubular fabric connector is formed from a single braided thread.

11. The occlusion device of claim 1 further comprising:
    a grasping knob attached to the proximal hub.

\* \* \* \* \*